(12) United States Patent
Kim

(10) Patent No.: US 10,383,515 B2
(45) Date of Patent: Aug. 20, 2019

(54) METHOD OF DETECTING PUPIL CENTER

(71) Applicant: 3E CO., LTD., Seongnam-si, Gyeonggi-do (KR)

(72) Inventor: Min Ho Kim, Seongnam-si (KR)

(73) Assignee: 3E CO., LTD., Seongnam-si (KR)

(\*) Notice: Subject to any disclaimer, the term of this patent is extended or adjusted under 35 U.S.C. 154(b) by 0 days.

(21) Appl. No.: 15/632,883

(22) Filed: Jun. 26, 2017

(65) Prior Publication Data

US 2018/0153397 A1 Jun. 7, 2018

(30) Foreign Application Priority Data

Dec. 7, 2016 (KR) .................. 10-2016-0166127

(51) Int. Cl.
| | | |
|---|---|---|
| *A61B 3/113* | (2006.01) | |
| *G06K 9/00* | (2006.01) | |
| *G06T 7/73* | (2017.01) | |

(52) U.S. Cl.
CPC .......... *A61B 3/113* (2013.01); *G06K 9/0061* (2013.01); *G06K 9/00597* (2013.01); *G06T 7/74* (2017.01); *G06T 2207/30041* (2013.01)

(58) Field of Classification Search
CPC .. A61B 3/113; G06K 9/0061; G06K 9/00597; G06T 7/74; G06T 2207/30041
USPC ........................................ 382/117
See application file for complete search history.

(56) References Cited

U.S. PATENT DOCUMENTS

| | | | |
|---|---|---|---|
| 2002/0154794 A1 | 10/2002 | Cho | |
| 2008/0069410 A1* | 3/2008 | Ko ............... | G06K 9/0061 |
| | | | 382/117 |
| 2008/0159600 A1 | 7/2008 | Cho | |

(Continued)

FOREIGN PATENT DOCUMENTS

| | | |
|---|---|---|
| KR | 10-2002-0071330 A | 9/2002 |
| KR | 10-0950138 B1 | 3/2010 |

(Continued)

OTHER PUBLICATIONS

Notice of Allowance issued by the Korean Intellectual Property Office for corresponding Korean Patent Application No. 10-2016-0166127, dated Mar. 8, 2018.

(Continued)

*Primary Examiner* — Wesley J Tucker
(74) *Attorney, Agent, or Firm* — Patent Office of Dr. Chung Park

(57) ABSTRACT

The method includes receiving an image of a user's eye region, selecting pixels included in a central region of the image, calculating an average value of brightness values of a plurality of adjacent pixels among the pixels included in the central region, converting the plurality of adjacent pixels into one pixel having the average value as a brightness value, comparing the brightness values of the converted pixels with a critical value to binarize the converted pixels, so as to create a binarized image, detecting a row including a pixel located at an uppermost end of pixels corresponding to a pupil, from the binarized image and correcting the position of the central region such that the pupil is located at the center of the image, based on position information of the row including the pixel located at the uppermost end of the pixels corresponding to the pupil.

7 Claims, 13 Drawing Sheets

(56) References Cited

U.S. PATENT DOCUMENTS

2010/0061631 A1\* 3/2010 Omori ................ G06K 9/00234
  382/170
2015/0164319 A1 6/2015 Kim et al.
2016/0286092 A1\* 9/2016 Ohta .................... G06K 9/0061

FOREIGN PATENT DOCUMENTS

| KR | 100950138 B1 | 3/2010 |
| KR | 10-1164769 B1 | 7/2012 |
| KR | 101164769 B1 | 7/2012 |
| KR | 10-2015-0027393 A | 3/2015 |
| KR | 10-2015-0070802 A | 6/2015 |

OTHER PUBLICATIONS

International Search Report issued for corresponding International Patent Application No. PCT/KR2017/005843, dated Aug. 24, 2017.

\* cited by examiner

METHOD OF DETECTING PUPIL CENTER

This application claims priority from Korean Patent Application No. 10-2016-0166127 filed on Dec. 7, 2016 in the Korean Intellectual Property Office, the disclosure of which is incorporated herein by reference in its entirety.

BACKGROUND

1. Field of the Invention

The present invention relates to a method of detecting a pupil center, and, more particularly, to a method of detecting a pupil center in which an image of a user's eye region is binarized and then a pupil center is detected using the pixel information of the binarized image.

2. Description of the Related Art

In performing a user certification procedure using the iris image of a user, a process of finding a pupil center should be preceded before acquiring iris data. The reason for this is that the iris data is obtained by collecting data belonging to a circle having a predetermined radius from the center point of a pupil.

Here, the pupil, which is a circle-shaped empty space located at the center of an iris, refers to an organ that allows external light to reach a retina.

Conventionally, in order to find a pupil center from an iris image, a method of detecting the boundary between an iris and a pupil using a circular edge detector and then detecting the center of the pupil has been used. However, such a pupil center detection method has a problem in that detection time is long as well as detection accuracy is low, and thus it takes more time to recognize the iris.

Therefore, there has been a need for a new type of pupil center detection method that can accurately and quickly detect a pupil center in performing a user identification procedure using an iris image.

SUMMARY

Aspects of the present invention provide a method of detecting a pupil center, which can accurately and quickly detect a pupil center.

However, aspects of the present invention are not restricted to the one set forth herein. The above and other aspects of the present invention will become more apparent to one of ordinary skill in the art to which the present invention pertains by referencing the detailed description of the present invention given below.

According to an aspect of the present invention provides method of detecting pupil center, the method comprising: receiving an image of a user's eye region; selecting pixels included in a central region of the image of the user's eye region; calculating an average value of brightness values of a plurality of adjacent pixels among the pixels included in the central region, and converting the plurality of adjacent pixels into one pixel having the average value as a brightness value; comparing the brightness values of the converted pixels with a predetermined critical value to binarize the converted pixels, so as to create a binarized image; detecting a row including a pixel located at an uppermost end of pixels corresponding to a pupil, from the binarized image; and correcting the position of the central region such that the pupil is located at the center of the image of the user's eye region, based on position information of the row including the pixel located at the uppermost end of the pixels corresponding to the pupil.

According to an aspect of the present invention, wherein the step of converting the plurality of adjacent pixels into one pixel having the average value as a brightness value includes the steps of: selecting pixels included in a rectangular region having a predetermined size among the pixels included in the central region; calculating an average value of a central pixel in the rectangular region, pixels located at the outermost peripheries of the central pixel in up, down, left and right directions of the rectangular region, and pixels located at the outermost peripheries of the central pixel in diagonal directions of the rectangular region; and converting the pixels included in the rectangular region to one pixel having the average value as a brightness value.

According to an aspect of the present invention, wherein the step of selecting the pixels included in the rectangular region having a predetermined size among the pixels included in the central region includes the step of: selecting pixels included in a second rectangular region such that some of the pixels belonging to the first rectangular region are selected in an overlapping manner.

According to an aspect of the present invention, the method further comparing the brightness value of the converted pixels with a predetermined critical value to binarize the converted pixels, so as to create the binarized image, includes the steps of: creating a histogram using the brightness values of the converted pixels; determining brightness value m when hm−1+hm+hm+1 is a maximum value in the histogram; determining brightness value n when hn*(m−n)2 is a maximum value is a maximum value in the histogram; determining brightness value i when hi−1+hi+hi+1 is a maximum value between the brightness value m and the brightness value n; and setting the brightness value i to a predetermined critical value, wherein hm, hn, and hi are the number of pixels having the brightness value m, the number of pixels having the brightness value n, and the number of pixels having the brightness value I, respectively.

According to an aspect of the present invention, the method further comparing the brightness values of the converted pixels with the predetermined critical value, converting a pixel having a brightness value more than the predetermined critical value into a white pixel, and converting a pixel having a brightness value equal to or less than the predetermined critical value into a black pixel.

According to an aspect of the present invention, wherein the step of detecting a row including a pixel located at an uppermost end of the pixels corresponding to the pupil, from the binarized image, includes the steps of: sequentially searching a row including pixels having a brightness value of 0 downward from the uppermost row of the binarized image; determining the brightness value of a pixel adjacent to the pixel having a brightness of 0 when the row including the pixels having a brightness value of 0 is searched; and determining a row including a pixel having a brightness value of 0 and a pixel having a brightness value of 0 adjacent to the pixel having a brightness value of 0 as an uppermost row of rows including pixels of the pupil when the brightness value of a pixel adjacent to the pixel having a brightness value of 0 is 0 and a row away from the row including the pixel having a brightness of 0 includes a pixel having a brightness value of 0.

According to an aspect of the present invention, wherein the step of correcting the position of the central region such that the pupil is located at the center of the image of the user's eye region, includes the steps of: calculating an upper margin value, a lower margin value, a left margin value and a right margin value using position information of the size of the central region and the uppermost row including the pixels corresponding to the pupil in the image of the user's image; and correcting the position of the central region using the margin values.

According to an another aspect of the present invention provide apparatus for detecting pupil center, the method comprising receiving an image of a user's eye region; selecting pixels included in a central region of the image of the user's eye region; calculating an average value of brightness values of a plurality of adjacent pixels among the pixels included in the central region, and converting the plurality of adjacent pixels into one pixel having the average value as a brightness value; comparing the brightness values of the converted pixels with a predetermined critical value to binarize the converted pixels, so as to create a binarized image; detecting start and end points of a black pixel for each row including the black pixel, from the binarized image; detecting a pixel located at a rightmost side and a pixel located at a leftmost side using the position information of the start point and the end point; and determining the center point of the pixel located at the rightmost side and the pixel located at the leftmost side as a center of the pupil.

According to an aspect of the present invention, wherein the step of converting the plurality of adjacent pixels into one pixel having the average value as a brightness value includes the steps of: selecting pixels included in a rectangular region having a predetermined size among the pixels included in the central region; calculating an average value of brightness values of a central pixel in the rectangular region, pixels located at the outermost peripheries of the central pixel in up, down, left and right directions of the rectangular region, and pixels located at the outermost peripheries of the central pixel in diagonal directions of the rectangular region; and converting the pixels included in the rectangular region to one pixel having the average value as a brightness value.

According to an aspect of the present invention, wherein the step of selecting the pixels included in the rectangular region having a predetermined size among the pixels included in the central region includes the step of: selecting pixels included in a second rectangular region such that some of the pixels belonging to the first rectangular region are selected in an overlapping manner.

According to an aspect of the present invention, the method further comprising the steps of: comparing the brightness values of the converted pixels with a predetermined critical value to binarize the converted pixels, so as to create the binarized image, includes the steps of: creating a histogram using the brightness values of the converted pixels; determining brightness value m when hm−1+hm+hm+1 is a maximum value in the histogram; determining brightness value n when hn*(m−n)2 is a maximum value is a maximum value in the histogram; determining brightness value i when hi−1+hi+hi+1 is a maximum value between the brightness value m and the brightness value n; and setting the brightness value I to a predetermined critical value, wherein hm, hn, and hi are the number of pixels having the brightness value m, the number of pixels having the brightness value n, and the number of pixels having the brightness value I, respectively.

According to an aspect of the present invention, the method further comprising: comparing the brightness values of the converted pixels with the predetermined critical value, converting a pixel having a brightness value more than the predetermined critical value into a white pixel, and converting a pixel having a brightness value equal to or less than the predetermined critical value into a black pixel.

According to an aspect of the present invention, the method further comprising: creating an imaginary line extending vertically downward from the central pixel of the start row including the pixels corresponding to the pupil; calculating the error rate of the determined pupil center position by the shortest distance from the leftmost pixel to the imaginary line and the shortest distance from the rightmost pixel to the imaginary line; and determining that the determined pupil center is not an actual pupil center when the error rate exceeds a predetermined critical value.

According to an aspect of the present invention, wherein the step of calculating the error rate includes the step of: calculating the error rate using Math Formula below:

$$\frac{|X_{top} - X_L| - |X_{top} - X_R|}{|X_{top} - X_L| + |X_{top} - X_R|}$$

where $X_{top}$ is position information of the central pixel, $X_L$ is position information of the leftmost pixel, and $X_R$ is position information of the rightmost pixel.

According to an aspect of the present invention, the method further comprising: calculating a slope of a straight line connecting the leftmost pixel and the rightmost pixel; and determining that the determined pupil center is not an actual pupil center when the slope exceeds a predetermined critical value.

According to an aspect of the present invention, wherein the step of calculating the slope includes the step of: calculating the slope using Math Formula below:

$$\left|\frac{X_R - X_L}{m - n}\right|$$

where m is position information of a row at which the rightmost pixel is located, n is position information of a row at which the leftmost pixel is located, $X_L$ is position information of the leftmost pixel, and $X_R$ is position information of the rightmost pixel, and $X_L$ is position information of the leftmost pixel.

According to an another aspect of the present invention provide method of detecting a pupil center, the method comprising (a) receiving an image of a user's eye region; (b) selecting pixels included in a central region of the image of the user's eye region; (c) calculating an average value of brightness values of a plurality of adjacent pixels among the pixels included in the central region, and converting the plurality of adjacent pixels into one pixel having the average value as a brightness value; (d) comparing the brightness values of the converted pixels with a predetermined critical value to binarize the converted pixels, so as to create a binarized image; (e) detecting a row including a pixel located at an uppermost end of pixels corresponding to a pupil, from the binarized image; and (f) correcting the position of the central region such that the pupil is located at the center of the image of the user's eye region, with position information of the row including the pixel located at the uppermost end of the pixels corresponding to the pupil; (g) selecting pixels included in the corrected central region; (h) repeating the steps (c) and (d) with respect to the pixels included in the corrected central region; (i) detecting start and end points of a black pixel for each row including the black pixel, from the binarized image; (j) detecting a pixel located at a rightmost side and a pixel located at a leftmost side using the position information of the start point and the end point; and (k) determining the center point of the pixel located at the rightmost side and the pixel located at the leftmost side as a center of the pupil.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE EMBODIMENTS

Figure 1:
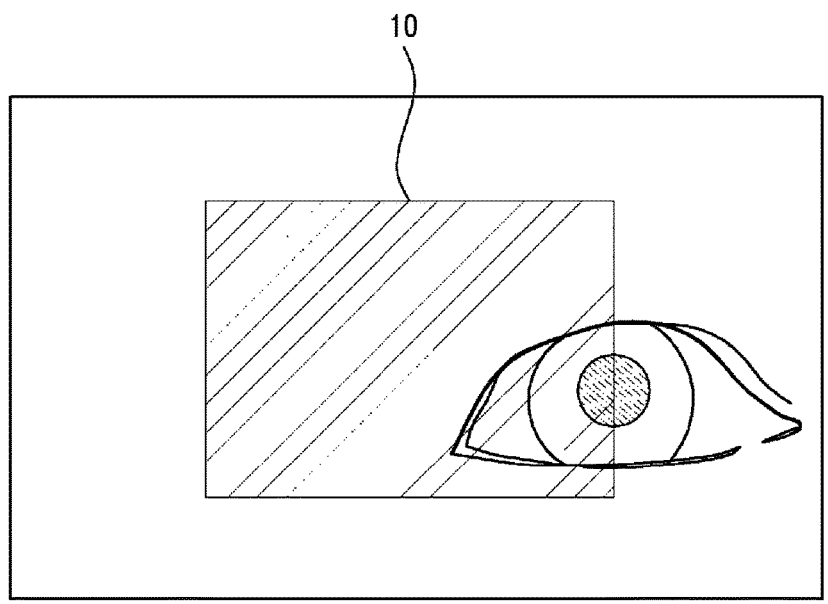
FIG. 1 is a view for explaining an image of a user's eye region.

Hereinafter, exemplary embodiments of the present disclosure will be described in detail with reference to the accompanying drawings. Advantages and features of the present disclosure and methods to achieve them will become apparent from the descriptions of exemplary embodiments herein below with reference to the accompanying drawings. However, the present invention is not limited to exemplary embodiments disclosed herein but may be implemented in various different ways. The exemplary embodiments are provided for making the disclosure of the present invention thorough and for fully conveying the scope of the present invention to those skilled in the art. It is to be noted that the scope of the present invention is defined only by the claims. Like reference numerals denote like elements throughout the descriptions.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Unless specifically mentioned otherwise, a singular form may include a plural form in the present specification. Throughout this specification, the word "comprise" and variations such as "comprises" or "comprising," will be understood to imply the inclusion of stated constituents, steps, operations and/or elements but not the exclusion of any other constituents, steps, operations and/or elements.

The method of detecting a pupil center according to an embodiment of the present invention is roughly divided into two steps. The first step is a step of finding the position of a pupil from the image of a user's eye region, and the second step is a step of detecting the center of the pupil.

In the method of detecting a pupil center according to an embodiment of the present invention, as shown in FIG. 1, an algorithm for detecting a pupil and acquiring iris data only to the central portion 10 of an image is applied, on the premise that the pupil is located at the center of the image of a user's eye region.

However, as shown in FIG. 1, when the pupil and iris are not located at the center of the image of the user's eye region, intact data cannot be acquired, and thus a pretreatment process of finding the position of a pupil from the image is required.

Hereinafter, the method of detecting a pupil center will be described based on the aforementioned two steps.

Step of Detecting Position of Pupil from Image of User's Eye Region

Figure 2:
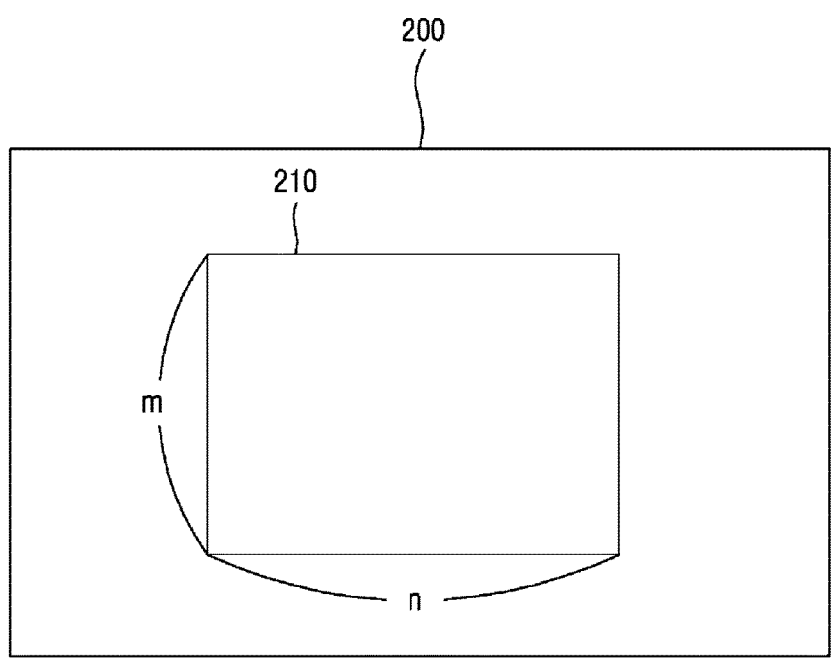
FIG. 2 is a view for explaining a process of selecting pixels included in a region presumed to have a pupil according to an embodiment of the present invention.

FIG. 2 is a view for explaining a process of selecting pixels included in a region presumed to have a pupil according to an embodiment of the present invention.

Hereinafter, for convenience of explanation, a subject performing each step will be omitted. However, each step to be described below may be performed by an electronic device in which a program for performing the method of detecting a pupil center is installed.

First, an image 200 in which a user's eye region is photographed is received. Then, pixels included in the central region 210 of the image 200 are selected. Since it is impossible to exactly know where the user's pupil is located in the initial stage of receiving the image of the user's eye region, the pixels included in the central region in which the pupil of the user is presumed to be located are selected.

The position information of the pixels included in the central region 210 and the brightness values of the respective pixels may be represented by the following matrix.

$$A = \begin{pmatrix} A_{1,1} & \cdots & A_{1,n} \\ \vdots & \ddots & \vdots \\ A_{m,1} & \cdots & A_{m,n} \end{pmatrix} \quad \text{[Math Formula 1]}$$

When there are pixels of m rows and n columns in the central region, the location information of each component of the matrix may be position information of each pixel, and the value of each component may be a brightness value of each pixel.

As described above, the information of the pixels included in the central region 210 is represented by matrix A, and separate matrix B, which is distinguished from the matrix A, is created using the matrix A.

Hereinafter, a process of generating matrix B using the matrix A will be described in detail.

Figure 3:
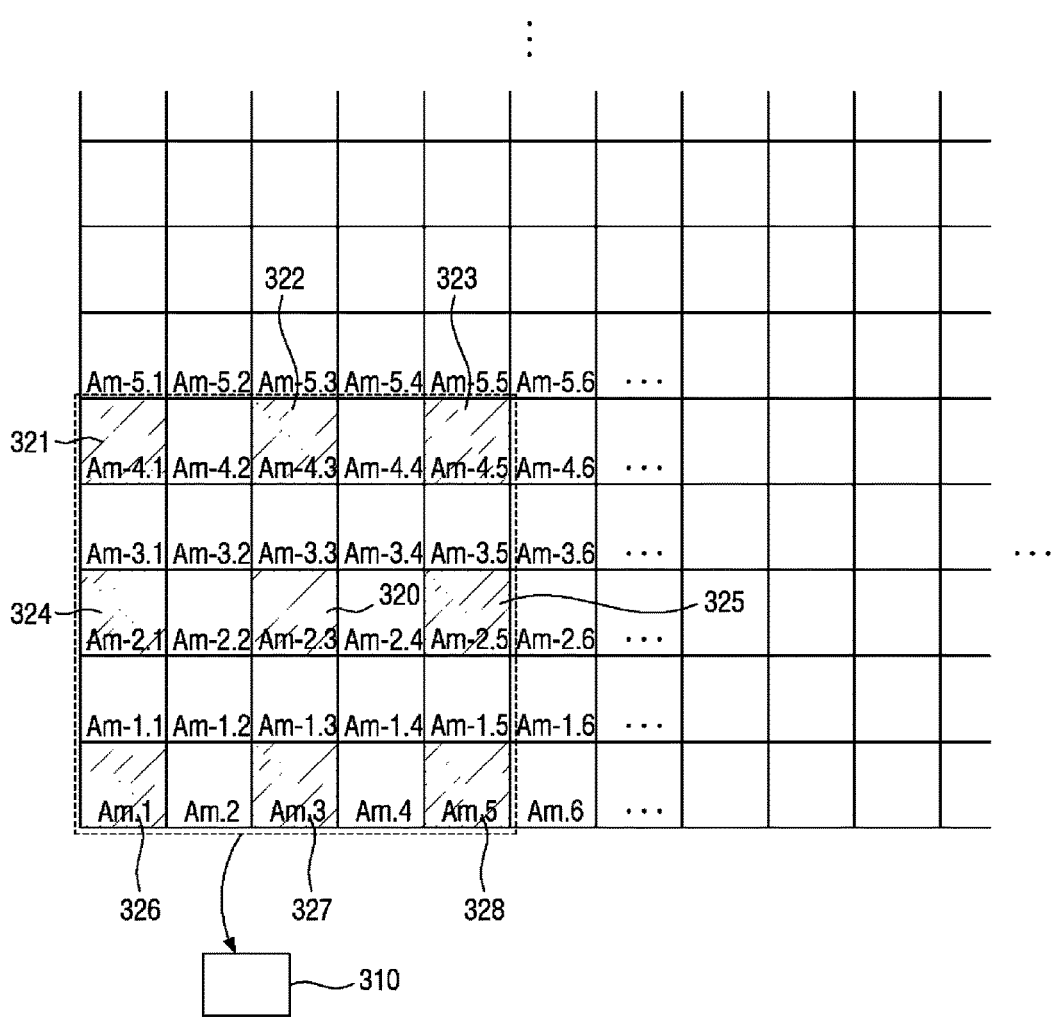
FIG. 3 is a view for explaining a process of generating another pixel with pixels included in a central region according to an embodiment of the present invention.

FIG. 3 is a view for explaining a process of generating another pixel with the pixels included in the central region according to an embodiment of the present invention.

FIG. 3 shows an enlarged view of the pixels included in the central region 210. Since the information of the pixels included in the central region 210 corresponds to the components of the above-described matrix A, the information of each of the pixels may be represented by the components of the matrix A as shown in FIG. 3.

In order to create the matrix B, first, an average value of brightness values of a plurality of adjacent pixels is calculated. And, the plurality of adjacent pixels is converted into one pixel having the average value as a brightness value.

For example, if the plurality of adjacent pixels are selected in a rectangular shape as shown in FIG. 3, 25 pixels included in the rectangular shape may be converted into one pixel having a predetermined brightness value. In this case, the brightness value of the converted pixel 310 may be an average brightness value of the selected 25 pixels.

In this case, in order to minimize an operation amount and efficiently use computing resources, only some of the plurality of adjacent pixels may be selected to calculate an average brightness value of the selected pixels.

For example, the average brightness value of a central pixel 320, pixels 322, 324, 325 and 327 located at the outermost peripheries of the central pixel 320 in up, down, left and right directions, and pixels 321, 323, 326 and 328 located at the outermost peripheries of the central pixel 320 in diagonal directions, among the pixels selected in a rectangular shape, is calculated.

And, the pixels selected in a rectangular shape may be converted into one pixel 310 having the average brightness value calculated in the above procedure as a brightness value.

The same process described with reference FIG. 3 is applied to other pixels belonging to the central region 210.

Figure 4:
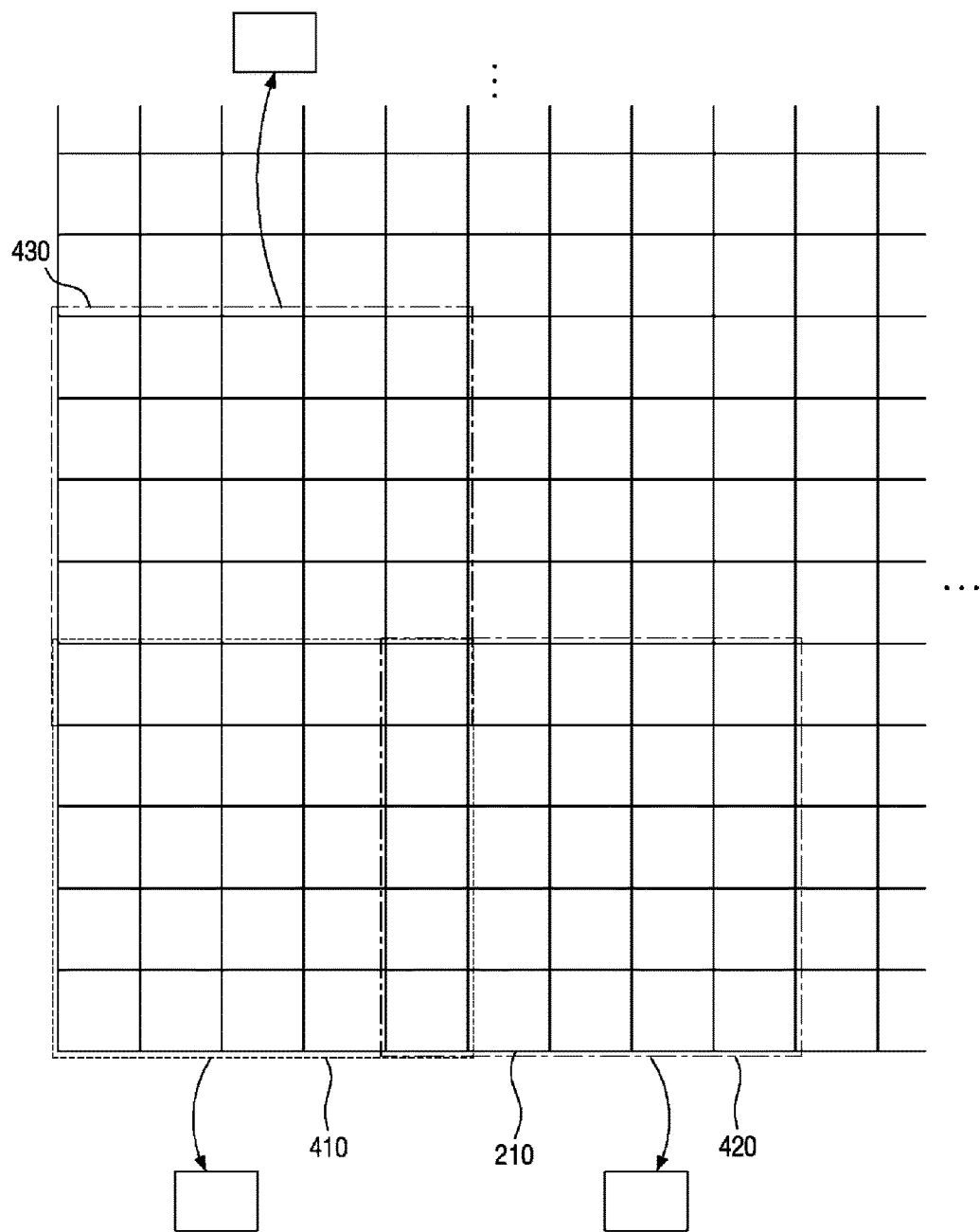
FIG. 4 is a view for explaining a process of converting pixels belonging to a central region into another pixel according to an embodiment of the present invention.

FIG. 4 is a view for explaining a process of converting pixels belonging to a central region 210 into another pixel according to an embodiment of the present invention.

In the method of detecting a pupil center according to an embodiment of the present invention, among the pixels belonging to the central region 210, a plurality of adjacent pixels is converted into one pixel. In this case, another plurality of pixels are selected to overlap some of the previously selected pixels, and then these pixels may also be converted into one pixel.

For example, if the first selected pixels are pixels belonging to a first rectangular region 410, pixels belonging to a second rectangular region 420 are selected to overlap some of the pixels belonging to the first rectangular region 410, and then the pixels belonging to the second rectangular region 420 are converted into one pixel.

In the method of converting the pixels belonging to the second rectangular region 420 into one pixel, as described with reference to FIG. 3, an average value of brightness values of all or some of the pixels belonging to the second rectangular region 420 is calculated, and these pixels are converted into one pixel having the average value as a brightness value.

Similarly, pixels belonging to a third rectangular region 430 are selected to overlap some of the pixels belonging to the first rectangular region 410, and then the pixels belonging to the third rectangular region 430 are converted into one pixel.

When the pixels belonging to the central region 210 is converted into another pixel by the aforementioned method, separate matrix B, which is distinguished from matrix A, is created by the matrix A representing the information of the pixels included in the central region 210.

Figure 5:
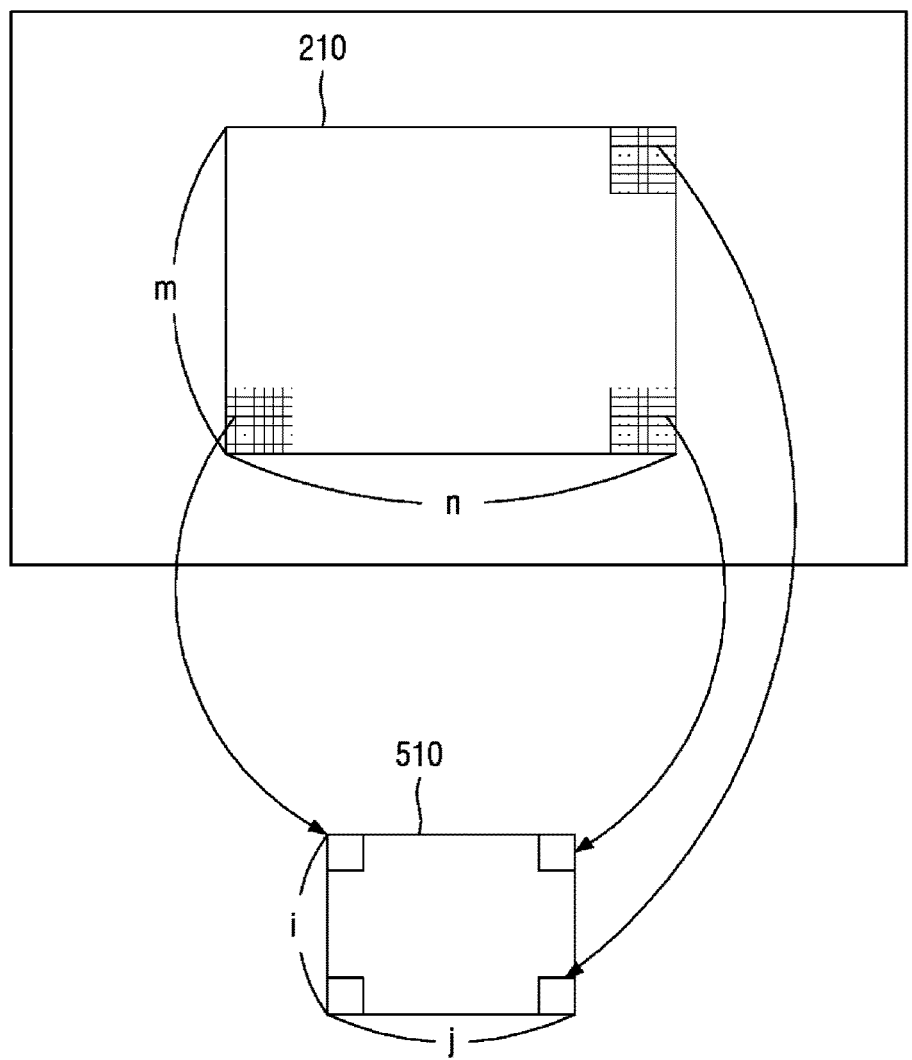
FIG. 5 is a view for explaining the result of converting pixels belonging to a central region according to an embodiment of the present invention.

FIG. 5 is a view for explaining the result of converting the pixels belonging to the central region according to an embodiment of the present invention.

When the process described with reference to FIGS. 3 and 4 is applied to the pixels belonging to the central region 210, a converted image 510 shown in FIG. 5 may be created. In this case, the position information of the pixels belonging to the central region 210 is converted into a position rotated 180°.

For example, a plurality of pixels belonging to the left lower end of the central region 210 are converted into one pixel located at the left upper end of the converted image 510, and a plurality of pixels belonging to the right lower end of the central region 210 are converted into one pixel located at the right upper end of the converted image 510.

Similarly, a plurality of pixels belonging to the right upper end of the central region 210 are converted into one pixel located at the right lower end of the converted image 510.

In this case, the position information of the pixels belonging to the converted image 510 and the brightness values of the respective pixels may be represented by the following matrix.

$$B = \begin{pmatrix} B_{1,1} & \cdots & B_{1,j} \\ \vdots & \ddots & \vdots \\ B_{i,1} & \cdots & B_{i,j} \end{pmatrix}$$ [Math Formula 2]

Since each pixel of the converted image 510 is generated by converting the plurality of pixels belonging to the central region 210 into one pixel, the number of pixels of the converted image 510 is smaller than the number of pixels belonging to the central region 210.

That is, the number m of rows in the matrix A is larger than the number i of rows in the converted matrix B, and the number n of columns in the matrix A is larger than the number j of columns in the converted matrix B.

The process of converting the pixels belonging to the central region 210 into the pixels of the converted image 510 by applying the processes of FIGS. 3 to 5 will be described as follows through Math Formulae.

It is exemplified in this embodiment that the number of pixels belonging to the central region 210 is 320×324, and the number of pixels belonging to the converted image 510 is 80×84.

[Math Formula 3]

$$B_{ij} = \frac{1}{9}\{(A_{m-2,n-2} + A_{m,n-2} + A_{m+2,n-2}) +$$

-continued $$(A_{m-2,n} + A_{m,n} + A_{m+2,n}) + (A_{m-2,n+2} + A_{m,n+2} + A_{m+2,n+2})\}$$

Here, M=430−4i, n=160+4j.

Each component of the matrix B converted by applying the above-described Math Formula 3 has one of the brightness values of 0 to 255.

In the method of detecting a pupil center according to an embodiment of the present invention, the brightness values of the components of the matrix B, that is, the pixels of the converted image 510 are compared with a predetermined critical value to binarize the converted pixels.

Here, the binarization of pixels means that a pixel having a brightness value more than a predetermined critical value according to the brightness values of the pixels is converted into a white pixel (a pixel having a brightness value of 255), and a pixel having a brightness value equal to or less than a predetermined critical value according to the brightness values of the pixels is converted into a black pixel (a pixel having a brightness value of 0).

For this purpose, a predetermined critical value must first be calculated using the component values of the matrix B.

Figure 6:
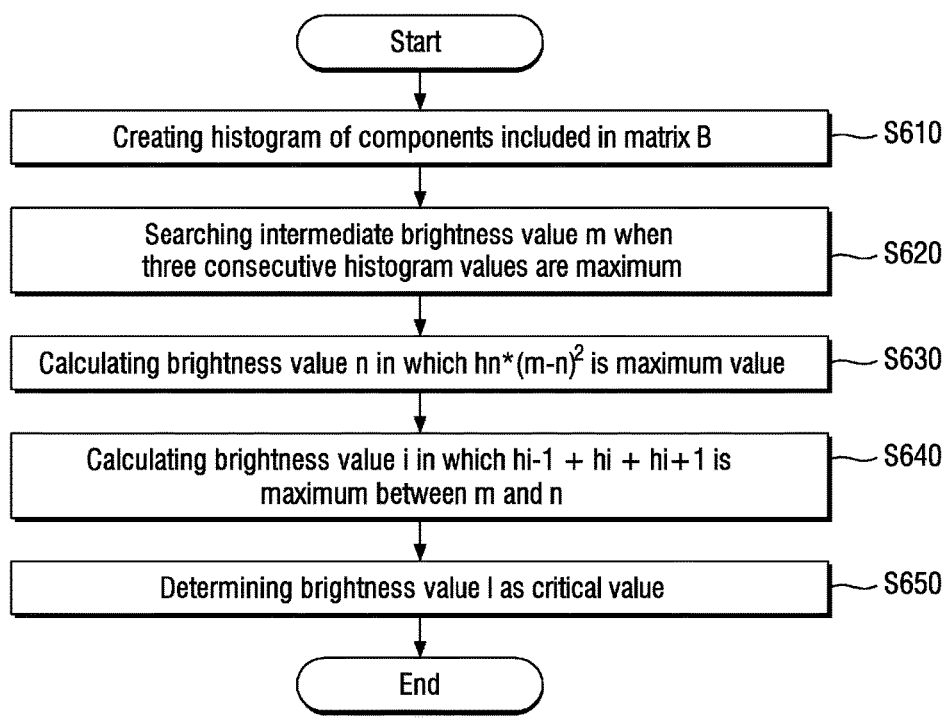
FIG. 6 is a flowchart for explaining a process of calculating a critical value using component values of matrix B according to an embodiment of the present invention.

FIG. 6 is a flowchart for explaining a process of calculating a critical value using the component values of the matrix B according to an embodiment of the present invention.

In order to calculate the critical value, a histogram of the components included in the matrix B is created (S610). Specifically, the histogram means the number of components having respective brightness values from 0 to 255 among the components included in the matrix B.

For example, $h_0$ is the number of components having a brightness value of 0, $h_1$ is the number of components having a brightness value of 1, and $h_2$ is the number of components having a brightness value of 2. Through the aforementioned method, the histogram is created by obtaining the number of components having respective brightness values from 0 to 255.

Then, when the sum of three consecutive histogram values is the maximum value, an intermediate brightness value is searched (S620). This relation is represented by the following Math Formula 4.

$$h_{max,1} = h_{m-1} + h_m + h_{m+1} \quad \text{[Math Formula 4]}$$

That is, when $h_{max,1}$ is the maximum value, value m is searched.

Next, when $h_{max,2}$, calculated by the following Math Formula 5, has the maximum value, brightness value n is calculated (S630).

$$h_{max,2} = h_n * (m-n)^2 \quad \text{[Math Formula 5]}$$

When brightness value m and brightness value n are calculated, brightness value i satisfying the following Math Formula 6 between the brightness value m and the brightness value n is calculated (S640).

$$h_{max} = h_{i-1} + h_i + h_{i+1} \quad \text{[Math Formula 6]}$$

That is, three brightness values having the maximum value of the sum of three consecutive histograms between the brightness value m and the brightness value n are calculated, and the intermediate value therebetween is determined as i.

The brightness value i calculated through the above process is determined as a critical value (S650).

That is, among the components included in the matrix B, the components whose component values are more than the value i are converted into white pixels, and the components whose component values are equal to or less than the value i are binarized into black pixels.

According to expectation, after the binarization is completed, the pixels corresponding to the pupil in the central region 210 are converted into black pixels, and the pixels corresponding to the portion other than the pupil in the central region 210 are converted into white pixels.

Then, the position of a pupil is searched from the binarized image.

Figure 7:
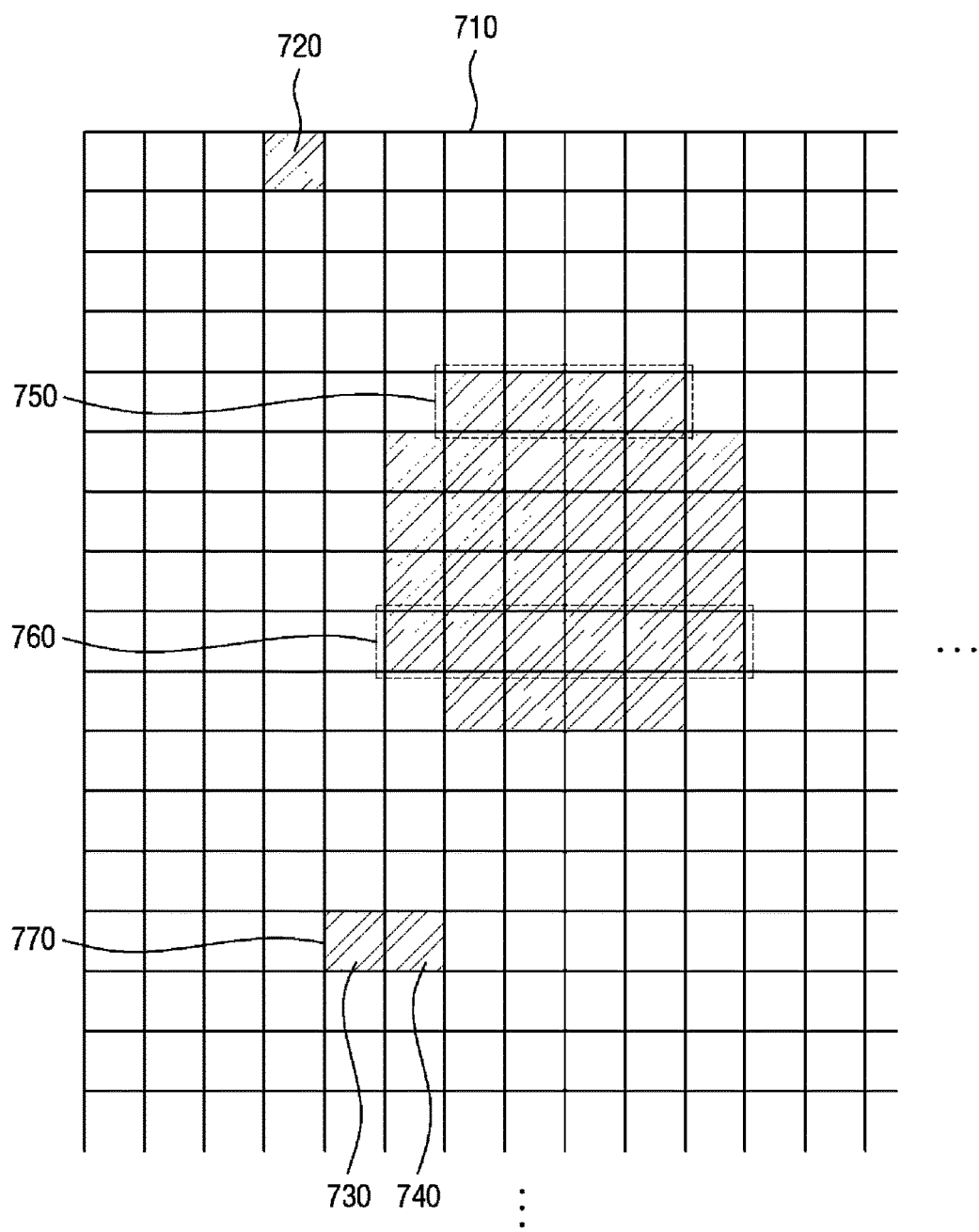
FIG. 7 is a view for explaining a process of searching the position of a pupil from a binarized image according to an embodiment of the present invention.

FIG. 7 is a view for explaining a process of searching the position of a pupil from the binarized image according to an embodiment of the present invention.

The purpose of the step to be illustrated in FIG. 7 is not to search all the pixels corresponding to the pupil in the binarized image but to find the pixels located at the uppermost end of the binarized image, among the pixels corresponding to the pupil.

For this purpose, a row including pixels having a brightness value of 0 is sequentially searched downward from the uppermost row of the binarized image 710. For example a row including pixels having a brightness value of 0, that is, black pixels is searched in order of first row, second row, and third row.

When a row including pixels having a brightness value of 0 is searched, the brightness value of a pixel having a brightness value of 0 in the row and the brightness value of a pixel adjacent thereto in the row are determined. For example, when it is determined that the brightness value of the pixel located in the $i^{th}$ row and the $j^{th}$ column is 0, the brightness value of the pixel located in the $i^{th}$ row and the $(j+1)^{th}$ column is determined.

When the brightness value of an adjacent pixel is not 0, it is determined that the pixel included in the row is not a pixel corresponding to the pupil. In FIG. 7, in the case of the row including the first pixel 720, the brightness value of the first pixel is 0, but the brightness value of the pixel adjacent thereto is not 0. Therefore, it is determined that the row including the first pixel 720 is a row not including the pixel corresponding to the pupil.

When a row including adjacent pixels having a brightness value of 0 is searched, next, it is determined whether pixels having a brightness value of 0 are adjacent to each other in a row away from the row by a predetermined number of rows.

For example, in FIG. 7, since a pixel having a brightness value of 0 exists in the $x^{th}$ row 750 and a pixel adjacent to the pixel also has a brightness value of 0, it is determined whether pixels having a brightness value of 0 are adjacent to each other in the $y^{th}$ row 760 away from the $x^{th}$ row 750 by a predetermined number of rows.

Since pixels having a brightness value of 0 are adjacent to each other even in the $y^{th}$ row 760, in this case, it is determined that the $x^{th}$ row is the uppermost row including the pixels corresponding to the pupil.

On the other hand, in the case of the $z^{th}$ row 770, since pixels having a brightness value of 0 are adjacent to each other in the $z^{th}$ row but pixels having a brightness value of 0 do not exist in a row away from the $z^{th}$ row 770 by a predetermined number of rows, it is determined that the $z^{th}$ row 770 does not include the pixels corresponding to the pupil.

The uppermost row among the rows including the pixels of the pupil in the binarized image 710 may be detected through the above process.

When the uppermost row including the pixels of the pupil is detected from the binarized image 710, it is possible to detect the position of the pupil in the image 200 in which a user's eye region is photographed.

When the position of the pupil is detected from the image 200 in which a user's eye region is photographed, the position of the central region 210 may be corrected such that the pupil is located at the center of the central region 210.

Figure 8:
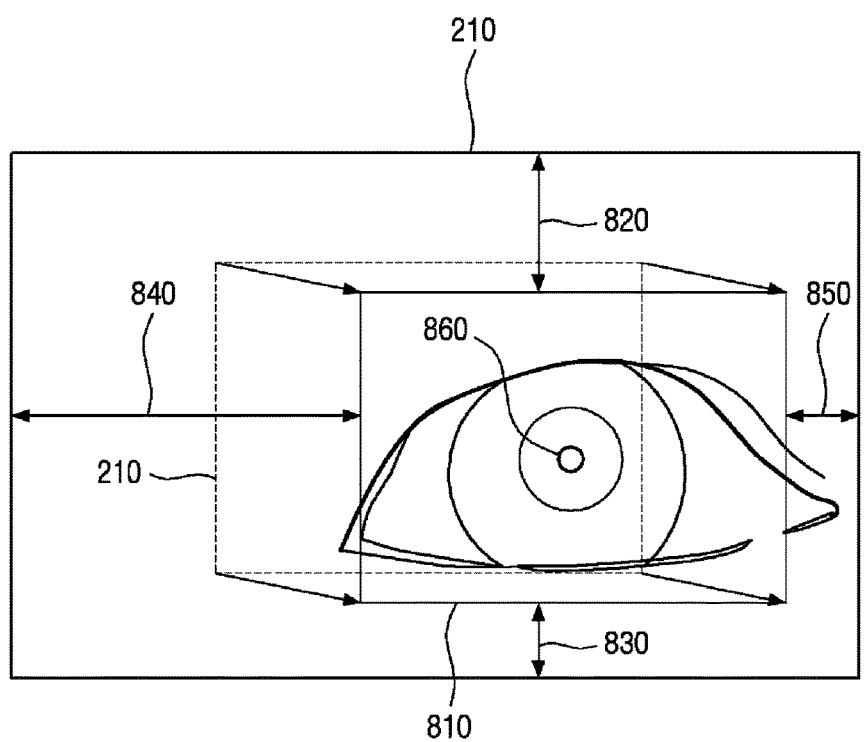
FIG. 8 is a view for explaining a process of correcting the position of a central region according to an embodiment of the present invention.

FIG. 8 is a view for explaining a process of correcting the position of the central region according to an embodiment of the present invention.

When the uppermost portion of the pupil is detected in the central region 210, the position of the central region 210 is corrected such that the pupil portion is located at the center. Additionally, the size of the central region 210 may be corrected.

Specifically, an upper margin value 820, a lower margin value 830, a left margin value 840, and a right margin value 850 are calculated such that the pupil is located at the center of the corrected central region 810 in the image 200 in which the user's eye region is photographed.

Since the position of the pupil in the image 200 in which the user's eye region is photographed is determined by detecting the uppermost row including the pixels of the pupil, the upper margin value 820, the lower margin value 830, the left margin value 840, and the right margin value 850 may be calculated when using the information about the position of the pupil, the size of the corrected central region 810, and the size of the image 200 in which the user's eye region is photographed.

Since the corrected center region 810 includes the entire pupil image of a user, the center of the pupil can now be detected. Hereinafter, a process of finding the center of the pupil using the information of the pixels included in the corrected central region 810 will be described.

Step of Detecting Pupil Center

Figure 9:
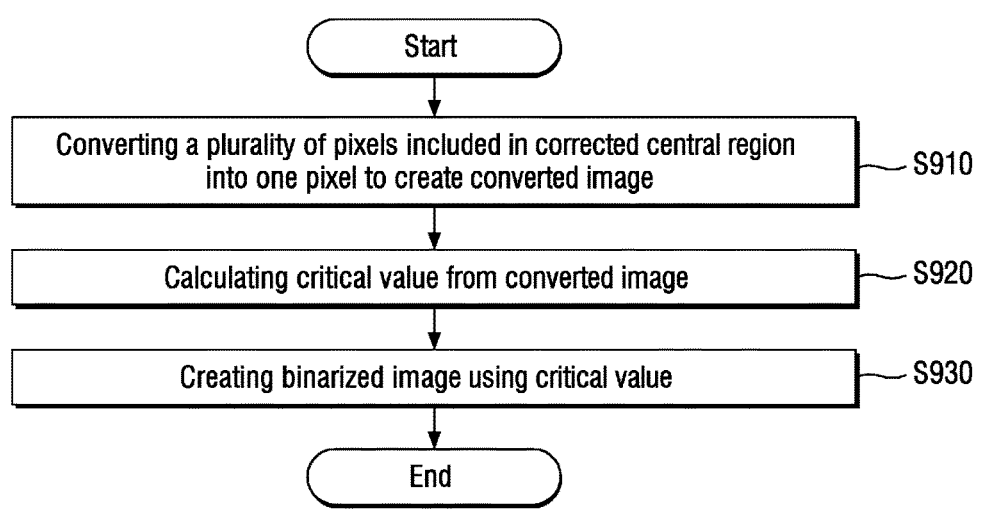
FIG. 9 is a flowchart for explaining a process of creating a binarized image using pixel information included in the corrected central region.

FIG. 9 is a flowchart for explaining a process of creating a binarized image using the pixel information included in the corrected central region.

Since the process of creating a binarized image using the pixel information included in the corrected central region is the same as the aforementioned process described with reference to FIGS. 2 to 6, this process will be briefly summarized and described while omitting duplicate descriptions.

First, a plurality of pixels included in the corrected central region 810 is converted to create a converted image (S910). The process of converting a plurality of pixels into one pixel to create a converted image is the same as the process described with reference to FIGS. 2 to 5.

Next, the process of calculating a critical value in order to binarize the converted image (S920) is the same as the process described with reference to FIG. 6. Similarly, the process of creating a binarized image using the calculated critical value (S930) is the same as the process described with reference to FIG. 6.

When the binarized image is created from the pixel information included in the corrected central region 810 through the aforementioned process, the center of the pupil is detected from the binarized image.

Figure 10:
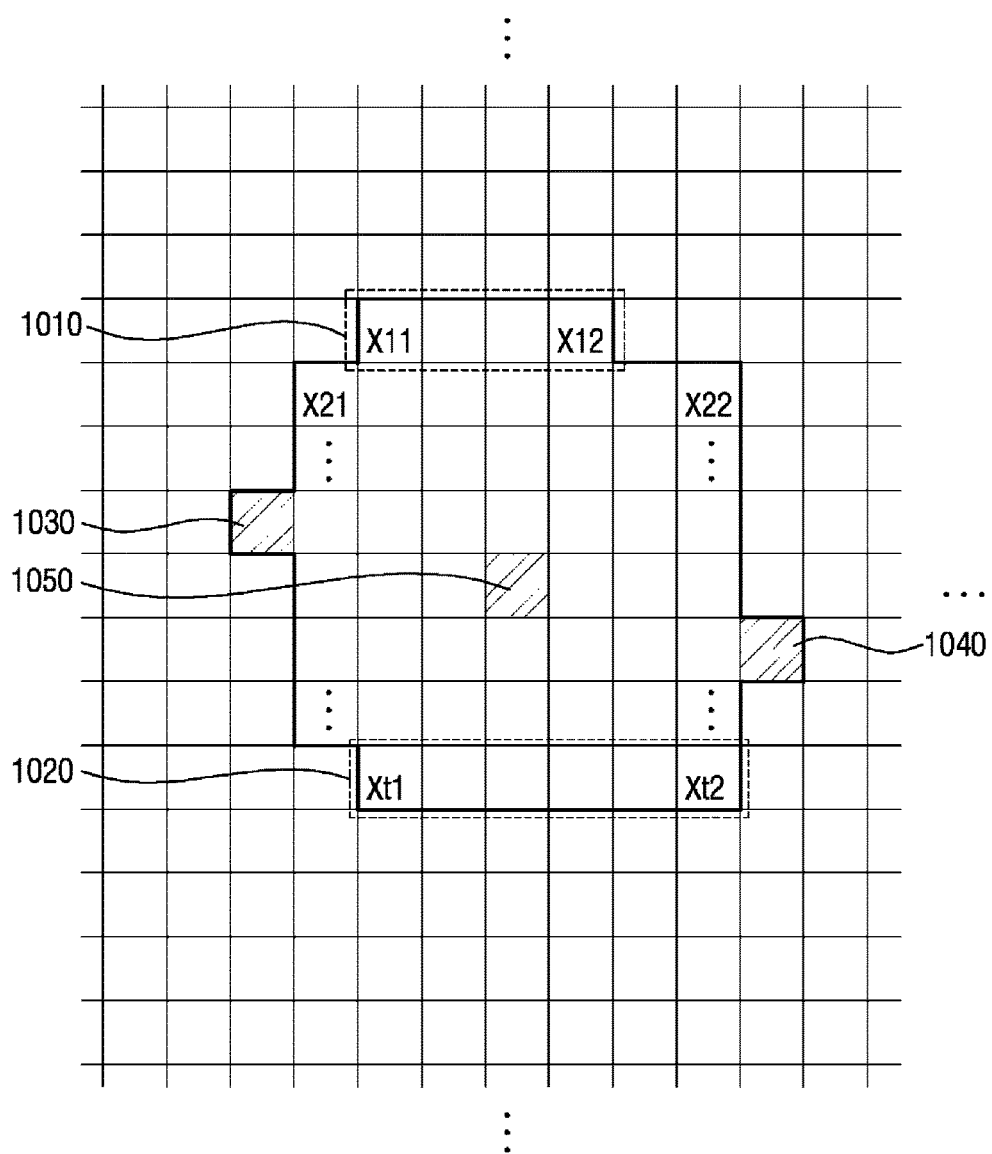
FIG. 10 is a view for explaining a process of detecting the center of a pupil from a binarized image according to an embodiment of the present invention.

FIG. 10 is a view for explaining a process of detecting the center of the pupil from the binarized image according to an embodiment of the present invention.

In FIG. 10, the pixels existing in the bold solid line are portions corresponding to the pupil. In the method of detecting a pupil center according to an embodiment of the present invention, Position information of the start point and end point of black pixels is detected for each row including the black pixels, and then matrix X is created using the position information.

That is, the matrix X is a matrix having position information of the start and end points of each row from a start row 1010 to an end row 1020 where pixels correspond to the pupil.

In this case, if the number of rows from the start row 1010 to the end row 1020 is t, the matrix X becomes a matrix of tx2. This matrix X is represented by the following Math Formula 7.

$$X = \begin{pmatrix} x_{11} & x_{12} \\ \vdots & \vdots \\ x_{t1} & x_{t2} \end{pmatrix}$$ [Math Formula 7]

As described above, the component values of the matrix X represent position information of the start point and end point of each row.

For example, $x_{11}$ indicates the position information of the pixel located at the leftmost of the black pixels included in the first row, and $x_{12}$ indicates the position information of the pixel located at the rightmost of the black pixels included in the first row. Similarly, $x_{t1}$ indicates the position information of the pixel located at the leftmost of the black pixels included in the $t^{th}$ row, and $x_{t2}$ indicates the position information of the pixel located at the rightmost of the black pixels included in the $t^{th}$ row.

Accordingly, when the component values of the matrix X are compared with each other, the position information of the pixel located at the leftmost of the component values belonging to the first column and the position information of the pixel located at the rightmost of the component values belonging to the second column may be detected.

The pixel located at the leftmost of FIG. 10 is a fourth pixel 1030, and the pixel located at the rightmost of FIG. 10 is a fifth pixel 1040. Therefore, the position information of the fourth pixel 1030 and the fifth pixel 1040 may be known through the above process.

Meanwhile, when a plurality of pixels are located at the leftmost of FIG. 10, or when a plurality of pixels exist at the rightmost of FIG. 10, a pixel belonging to the lowermost row may be selected as the leftmost or rightmost pixel.

If the position information of the fourth pixel 1030 is referred to as $(X_L, Y_L)$ and the position information of the fifth pixel 1040 is referred to as $(X_R, Y_R)$, the position information of the center of the pupil may be determined by the following Math Formula 8.

$$\left( \frac{X_L + X_R}{2}, \frac{Y_L + Y_R}{2} \right)$$ [Math Formula 8]

That is, the center of the line connecting the leftmost pixel and the rightmost pixel is determined as the center of the pupil.

However, since the position of the pupil center determined through the above process is an approximate value, If it is determined that the difference between the position of the pupil center determined through Math Formula 8 and the actual position of the pupil center exceeds a predetermined critical value, the center of the pupil is determined to be not able to be found in the corresponding image, and thus the center of the pupil should be detected from another image of the user's eye region.

Figure 11:
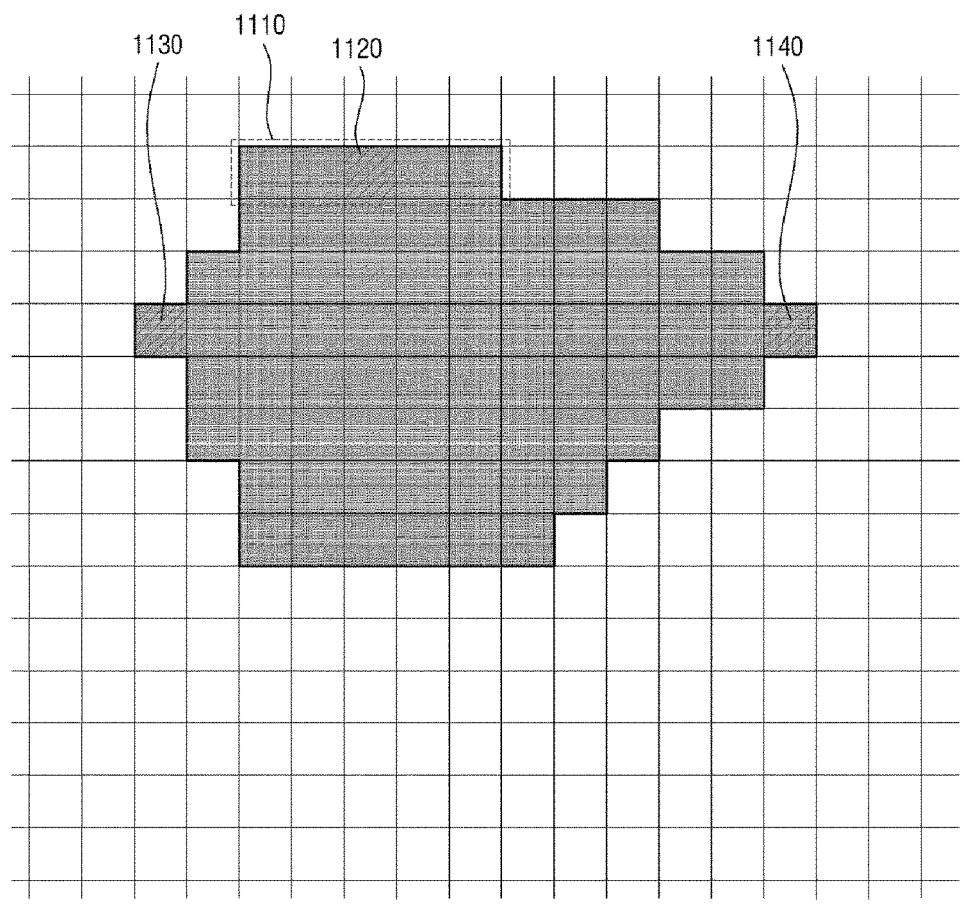
FIG. 11 is a view for explaining a process of verifying the position of a pupil center determined according to an embodiment of the present invention.

FIG. 11 is a view for explaining a process of verifying the position of the pupil center determined according to an embodiment of the present invention.

If the leftmost pixel and rightmost pixel detected through the process described with reference to FIG. 10 are spaced apart from each other by the same distance with respect to the center line, it can be determined that the position of the pupil center determined by Math Formula 8 approximates to the actual position of the pupil center. Here, the center line means an imaginary line extending vertically downward from the central pixel 120 of the start row 1110.

However, as shown in FIG. 11, when the leftmost pixel 1130 and the rightmost pixel 1140 are spaced apart from each other by different distances from each other, it can be determined that the position of the pupil center determined by Math Formula 8 is different from the actual position of the pupil center.

For this purpose, in the method of detecting the pupil center according to an embodiment of the present invention, it may be determined that, if an error rate is calculated by the following Math Formula 9 and the calculated error rate exceeds a predetermined critical value, the calculated position of the pupil center is not accurate.

$$오차율 = \frac{|X_{top} - X_L| - |X_{top} - X_R|}{|X_{top} - X_L| + |X_{top} - X_R|} \times 100 \quad \text{[Math Formula 9]}$$

Here, $X_{top}$ is the positional information of the central pixel 1120 of the start line 1110, $X_L$ is the positional information of the leftmost pixel 1130, and $X_R$ is the positional information of the rightmost pixel 1140.

It means that, as the above error rate increases, the distance difference between the position of the leftmost pixel 1130 from the center line and the position of the rightmost pixel 1140 from the center line from the center line increases. That is, it means that black pixels are not symmetrical with respect to the center line.

Generally, black pixels corresponding to the pupil are configured to be symmetrical left and right with respect to the pupil center. In this case, since the larger error rate means that the left and right sides are not symmetrical with respect to the pupil center, the error with the actual position of the pupil center increases when the position information of the leftmost pixel 1130 and the rightmost pixel 1140 is calculated in this state.

Therefore, in the method of detecting a pupil center according to an embodiment of the present invention, it is determined that the position of the pupil center is not accurate when the error rate exceeds a predetermined critical value.

The position of a pupil center may be verified by using the slope of the line connecting the leftmost pixel 1130 and the rightmost pixel 1140 in addition to the aforementioned method.

Figure 12:
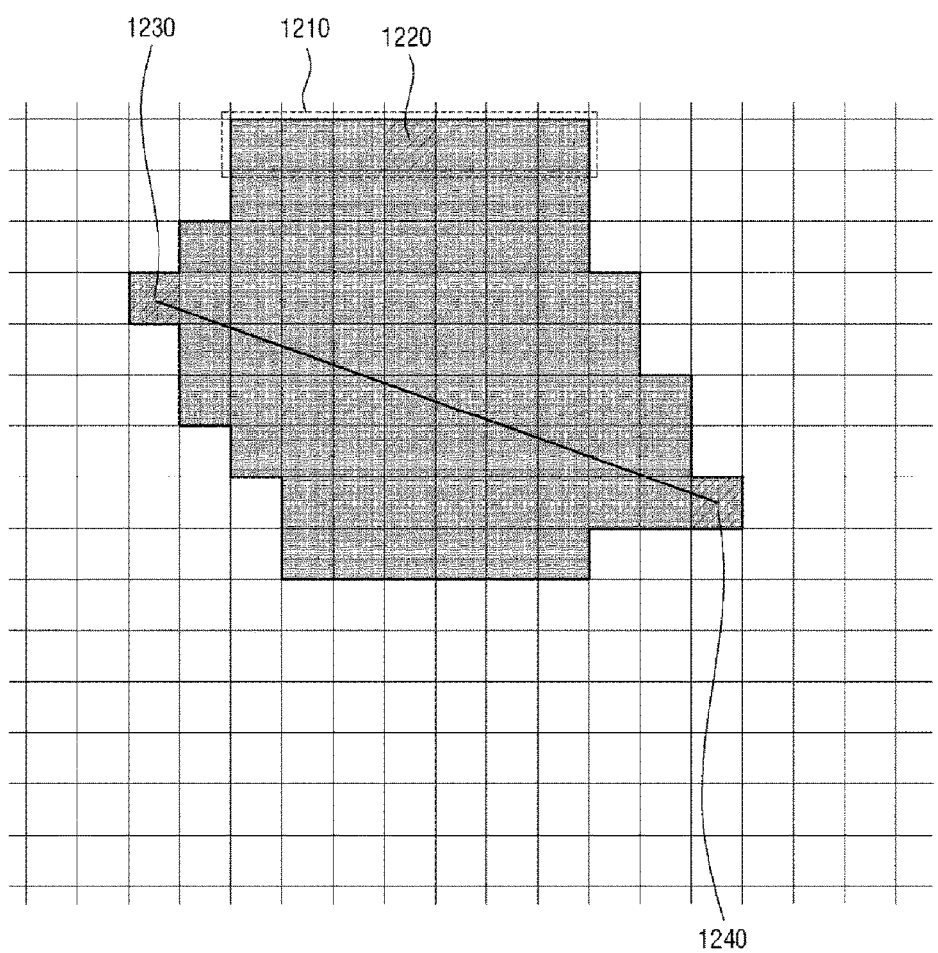
FIG. 12 is a view for explaining a process of verifying the position of a pupil center determined according to another embodiment of the present invention.

FIG. 12 is a view for explaining a process of verifying the position of a pupil center determined according to another embodiment of the present invention.

It may be determined that the position of the pupil center determined by Math Formula 8 is close to the actual position of the pupil center when the leftmost pixel and the rightmost pixel detected in the process described with reference to FIG. 10 are located in one row.

However, as shown in FIG. 12, when a row in which the leftmost pixel is located is far away from a row in which the rightmost pixel is located, the position of the pupil center determined by Math Formula 8 is greatly different from the actual position of the pupil center.

For this purpose, in the method of detecting the pupil center according to an embodiment of the present invention, it may be determined that, if the slope of the line connecting the leftmost pixel 1230 and the rightmost pixel 1240 is calculated by the following Math Formula 10 and the slope exceeds a predetermined critical value, the pupil center is not accurate.

$$기울기 = \left| \frac{X_R - X_L}{m - n} \right| \quad \text{[Math Formula 10]}$$

Here, m is the position information of a row in which the rightmost pixel 1240 is located, n is the position information of a row in which the leftmost pixel 1230 is located, $X_R$ is the position information of the rightmost pixel 1240, and $X_L$ is the leftmost pixel 1230.

As the row in which the leftmost pixel 1230 is located is farther away from the row in which the rightmost pixel 1240 is located, the position of the pupil center determined using the position information of the leftmost pixel 1230 and the rightmost pixel 1240 is not accurate. Therefore, it is determined that the position of the pupil center is not accurate if the slope exceeds a predetermined critical value.

In the method of detecting the pupil center according to an embodiment of the present invention, when it is determined that the pupil center is not accurate in at least one of the two verification methods described with reference to FIGS. 11 and 12, it is determined that the pupil center is not found in the corresponding image. Therefore, in this case, the pupil center may be detected in another image of a user's eye region.

Therefore, according to the method of detecting a pupil center, it is possible to accurately detect the pupil center.

Figure 13:
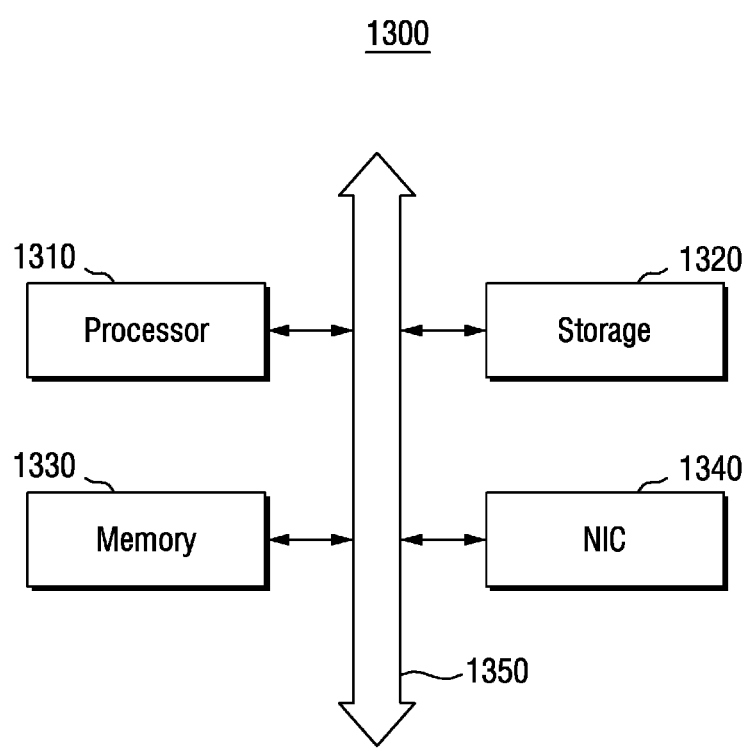
FIG. 13 is a block diagram illustrating an apparatus for detecting a pupil center according to an exemplary embodiment of the present disclosure.

FIG. 13 is a block diagram illustrating an apparatus for detecting a pupil center according to an exemplary embodiment of the present disclosure.

An apparatus for detecting a pupil center 1300 shown in FIG. 13 includes a processor 1310, a storage 1320, memory 1330, a network interface card (NIC) 1340, and a bus 1350.

The processor 1310 executes a program for detecting a pupil center. However, the program executed on the processor 1310 is not limited thereto but may include other general-purpose programs.

The storage 1320 stores the program for detecting a pupil center therein. According to an exemplary embodiment of the present disclosure, the program for detecting a pupil center, when executed, causes a computer to perform the operations of: receiving an image of a user's eye region; selecting pixels included in a central region of the image of the user's eye region; calculating an average value of brightness values of a plurality of adjacent pixels among the pixels included in the central region, and converting the plurality of adjacent pixels into one pixel having the average value as a brightness value; comparing the brightness values of the converted pixels with a predetermined critical value to binarize the converted pixels, so as to create a binarized image; detecting a row including a pixel located at an uppermost end of pixels corresponding to a pupil, from the binarized image; and correcting the position of the central region such that the pupil is located at the center of the image of the user's eye region, based on position information of the row including the pixel located at the uppermost end of the pixels corresponding to the pupil.

The memory 1330 may load the program for detecting a pupil center so that the program is executed on the processor 1310.

The network interface card (NIC) 1340 may be connected to a computing device.

The bus 1350 works as a data transfer path among the processor 1310, the storage 1320, the memory 1330, and the network interface card (NIC) 1340.

The above-described method may be implemented as a program that can be executed by a computer, and may be embodied in a computer-readable storage medium to be performed in a general-purpose digital computer that executes the program. In addition, the structure of the data used in the above-described method may be written on a computer-readable storage medium through various means. The computer-readable storage medium includes a storage medium such as a magnetic storage medium (e.g., a ROM, a floppy disk, a hard disk, etc.), and an optical recording medium (e.g., CD-ROM, a DVD, etc.).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of detecting a pupil center, comprising the steps of:
   receiving an image of a user's eye;
   selecting a first image including a plurality of pixel groups in a central region of the image of the user's eye region;
   calculating an average brightness value of each of the plurality of pixel groups and converting each of the plurality of pixel groups into each one of pixels by reducing a resolution of the first image, wherein said each one of pixels has a calculated average brightness value;
   binarizing the converted each one of pixels to be a black pixel or a white pixel according to a magnitude of the average brightness value of the converted each one of pixels compared to a predetermined critical brightness value, thereby creating a binarized image having the black pixel or the white pixel;
   detecting start and end points of the black pixel for each row including a set of consecutive black pixels, among rows of pixels in the binarized image;
   detecting, in the row including the set of consecutive black pixels, a first black pixel located at a rightmost side from the center line of the binarized image and a second black pixel located at a leftmost side from the center line of the binarized image, using the position information of the start point and the end point;
   determining a center point between the first black pixel and the second black pixel as a center of the pupil;
   creating an imaginary line extending vertically downward from a central pixel of a row including a first set of consecutive black pixels in the binarized image; and
   calculating an error rate of the determined center of the pupil using a shortest distance from the first black pixel to the imaginary line and the shortest distance from the second black pixel to the imaginary line,
   wherein the step of calculating the error rate includes the step of: calculating the error rate using Math Formula below:

$$\frac{|X_{top} - X_L| - |X_{top} - X_R|}{|X_{top} - X_L| + |X_{top} - X_R|}$$

where Xtop is position information of the central pixel, $X_L$ is position information of the second black pixel, and $X_R$ is position information of the first black pixel.

2. The method of claim 1,
   wherein the step of converting each of the plurality of pixel groups into each one of pixels includes the steps of:
   selecting a plurality of pixels included in a first rectangular region having a predetermined size among a plurality of pixel groups included in the central region;
   calculating an average brightness values of a central pixel in the plurality of pixels of the first rectangular region, pixels located at the outermost peripheries of the central pixel in up, down, left and right directions of the rectangular region, and pixels located at the outermost peripheries of the central pixel in diagonal directions of the rectangular region; and
   converting the plurality of pixels included in the rectangular region to one pixel having the average brightness value.

3. The method of claim 2,
   wherein the step of selecting the plurality of pixels included in the first rectangular region having a predetermined size among the plurality of pixel groups included in the central region includes the step of:
   selecting pixels included in a second rectangular region such that some of the pixels belonging to the first rectangular region are overlapped with the pixels which is included in the second rectangular region.

4. The method of claim 1, further comprising the steps of:
   binarizing the converted each one of pixels to be a black pixel or a white pixel according to a magnitude of the average brightness value of the converted each one of pixels compared to a predetermined critical brightness value, thereby creating a binarized image having the black pixel or the white pixel, includes the steps of:
   creating a histogram using the average brightness value of the converted each one of pixels;
   determining the average brightness value m when $h_{m-1}+h_m+h_{m+1}$ is a maximum value in the histogram;
   determining the average brightness value n when $h_n*(m-n)^2$ is a maximum value is a maximum value in the histogram;
   determining the average brightness value i when $h_{i-1}+h_i+h_{i+1}$ is a maximum value between the average brightness value m and the average brightness value n; and
   setting the average brightness value I to a predetermined critical value,
   wherein $h_m$, $h_n$, and $h_i$ are the number of pixels having the average brightness value m, the number of pixels having the average brightness value n, and the number of pixels having the average brightness value I, respectively.

5. The method of claim 4, further comprising:
   comparing the average brightness values of the converted each one of pixels with the predetermined critical brightness value, converting a pixel having an average brightness value more than the predetermined critical value into a white pixel, and converting a pixel having an average brightness value equal to or less than the predetermined critical value into a black pixel.

6. The method of claim 1, further comprising:
calculating a slope of a straight line connecting the first black pixel and the second black pixel; and
determining that the determined center of the pupil is not an actual pupil center when the slope exceeds a predetermined critical value.

7. The method of claim 6,
wherein the step of calculating the slope includes the step of: calculating the slope using Math Formula below:

$$\left| \frac{X_R - X_L}{m - n} \right|$$

where m is position information of a row at which the rightmost pixel is located from the center line of the binarized image, n is position information of a row at which the leftmost pixel is located from the center line of the binarized image, $X_L$ is position information of the leftmost pixel from the center lime of the binarized image, and $X_R$ is position information of the rightmost pixel from the center lime of the binarized image.

* * * * *